United States Patent [19]

Yamato et al.

[11] Patent Number: 4,534,975
[45] Date of Patent: Aug. 13, 1985

[54] PHARMACEUTICAL COMPOSITION CONTAINING 24,25-DIHYDROXYCHOLECALCIFEROL IN METHODS OF TREATMENT

[75] Inventors: Hideyuki Yamato, Tokyo; Yuji Maeda, Nagareyama; Fumisato Yoshino; Kyoya Takahata, both of Tokyo; Masanori Ikuzawa, Tachikawa; Tadaaki Kato, Tokyo; Chikao Yoshikumi, Kunitachi, all of Japan

[73] Assignee: Kureha Kagaku Kogyo Kabushiki Kaisha, Tokyo, Japan

[21] Appl. No.: 656,760

[22] Filed: Oct. 1, 1984

Related U.S. Application Data

[62] Division of Ser. No. 620,923, Jun. 15, 1984, Pat. No. 4,501,738.

[30] Foreign Application Priority Data

Jun. 30, 1983 [JP] Japan ................... 58-119423
Jun. 30, 1983 [JP] Japan ................... 58-119424
Jun. 30, 1983 [JP] Japan ................... 58-119425
Jun. 30, 1983 [JP] Japan ................... 58-119426
Jun. 30, 1983 [JP] Japan ................... 58-119428

[51] Int. Cl.$^3$ ............................ A61V 31/59
[52] U.S. Cl. ............................ 514/730
[58] Field of Search ....................... 424/236

*Primary Examiner*—Stanley J. Friedman
*Attorney, Agent, or Firm*—Cushman, Darby & Cushman

[57] ABSTRACT

Disclosed is a pharmaceutical composition in dosage unit form which comprises a dosage effective for the treatment of pains and pyrexia, hypertension, hypotension, hyperlipemia, inflammatory diseases or diseases due to the functional accentuation of thrombocytes of a compound of 24,25-dihydroxycholecalciferol and a pharmaceutical acceptable carrier or diluent therefor.

2 Claims, No Drawings

PHARMACEUTICAL COMPOSITION CONTAINING 24,25-DIHYDROXYCHOLECALCIFEROL IN METHODS OF TREATMENT

This is a division of application Ser. No. 620,923, filed June 15, 1984, now U.S. Pat. No. 4,501,738.

SUMMARY OF THE INVENTION

In a first aspect of the present invention, there is provided a pharmaceutical composition in dosage unit form which comprises a dosage effective for the treatment of pains and pyrexia, hypertension, hypotension, hyperlipemia, inflammatory diseases or diseases due to the functional accentuation of thrombocytes of a compound of 24,25-dihydroxycholecalciferol and a pharmaceutical acceptable carrier or diluent therefor.

In a second aspect of the present invention, there is provided a method for the treatment of pains and pyrexia, hypertension, hypotension, hyperlipemia, inflammatory diseases or diseases due to the functional accentuation of thrombocytes, which comprises administering to a patient suffering from pains and pyrexia, hypertension, hypotension, hyperlipemia, inflammatory diseases or diseases due to the functional accentuation of thrombocytes an effective amount of a compound of 24,25-dihydroxycholecalciferol.

DETAILED DESCRIPTION OF THE INVENTION

The present invention relates to a pharmaceutical composition in dosage unit form which comprises a dosage effective for the treatment of pains and pyrexia, hypertension, hypotension, hyperlipemia, inflammatory diseases or diseases due to the functional accentuation of thrombocytes of a compound of 24,25-dihydroxycholecalciferol and a pharmaceutical acceptable carrier or diluent therefor, and relates to a method for the treatment of pains and pyrexia, hypertension, hypotension, hyperlipemia, inflammatory diseases or diseases due to the functional accentuation of thrombocytes, which comprises administering to a patient suffering from pains and pyrexia, hypertension, hypotension, hyperlipemia, inflammatory diseases or diseases due to the functional accentuation of thrombocytes an effective amount of a compound of 24,25-dihydroxycholecalciferol.

Concerning the diseases due to the functional accentuation of thrombocytes, recently, the number of cases accompanying the functional accentuation of the thrombocytes is in a rising tendency by the increase of the number of aged people and the Europeanization and Americanization of eating habits and of the social environment as the main factors, and among the treatments for diseases due to the functional accentuation of the thrombocytes, the anti-thrombotic treatment has been applied.

The diseases to which the anti-thrombotic treatment is applied are cerebo-vascular diseases such as cerebral infarct and transient paroxysmal cerebral ischemia, ischemic heart diseases such as myocardial infarction, thrombosis due to the use of artificial materials and organs such as artificial heart, artificial lung, artificial A-V shunt, artificial heart valves, artificial vessels and catheters, disturbance of smaller vessels such as thrombocytopenic thrombotic purpura and hemolytic anemia due to disturbance of smaller vessels and hyperthrombocytemia. In addition, the anti-thrombotic treatment is applied to the diseases to the state of which the functional accentuation of thrombocytes has some relationship, the diseases being diabetes mellitus, chronic nephritis, nephrosic syndrome, hypertension, multiple sclerosis, gestational toxicosis, cancers, paroxysmal nocturnal hemoglobinuria, Kawasaki disease, Raynaud's disease and various disturbances induced by vibration.

Although as the anti-thrombotic treatment, administration of some pharmaceutical compositions comprising dipyridamole, trapidil or ticlopidine is carried out, there is a problem in the point of side effects of such a drug.

As a result of the present inventors' studies on the endogenous substances present in healthy human body, of which the safety has been demonstrated, it has been found that 24,25-dihydroxycholecalciferol (hereinafter referred to as 24,25-$(OH)_2$-$D_3$) has various physiological activities, and the present inventors have already found out the following activities in 24,25-$(OH)_2$-$D_3$:

anti-hypercalcemic activity, anti-ulcerous activity, preventive activity from the reduction of immunofunction, regulative activity of the metabolism of magnesium, anti-hyperphospheremic activity, regulative activity of blood sugar and antitumour activity.

Subsequently, as a result of their continued studies on the physiological activity of 24,25-$(OH)_2$-$D_3$, an antipyretic activity and a sedative activity, a regulating activity of the blood pressure, an antihyperlipemic effect, an anti-inflammatory activity and a preventing activity of the functional accentuation of the thrombocytes without being accompanied by marked side effects has been found therein, and the present inventors have attained the present invention.

24,25-$(OH)_2$-$D_3$ is high in safety, has a suppressing activity on the central nervous system, a regulating activity of the blood pressure, an antihyperlipemic effect, an anti-inflammatory activity and a preventing activity of the functional accentuation of the thrombocytes and accordingly, is effective as an active ingredient of a pharmaceutical composition for the treatment of pains and pyrexia, hypertension, hypotension, hyperlipemia, inflammatory diseases or diseases due to the functional accentuation of thrombocytes.

Every one of 24,25-$(OH)_2$-$D_3$ is a substance publicly known and represented by one of the following formulae, and is disclosed, for instance, in "Vitamin D; Molecular Biology and Clinical Nutrition" by Anthony W. Norman, pages 1 to 92 (1980).

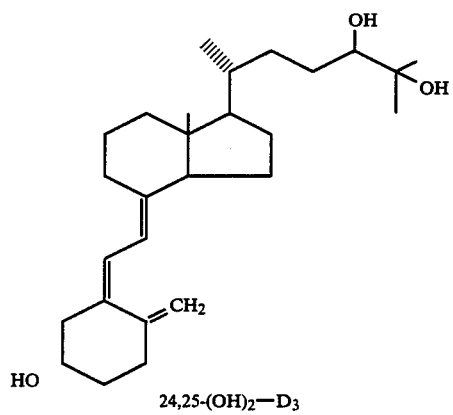

24,25-$(OH)_2$—$D_3$

-continued

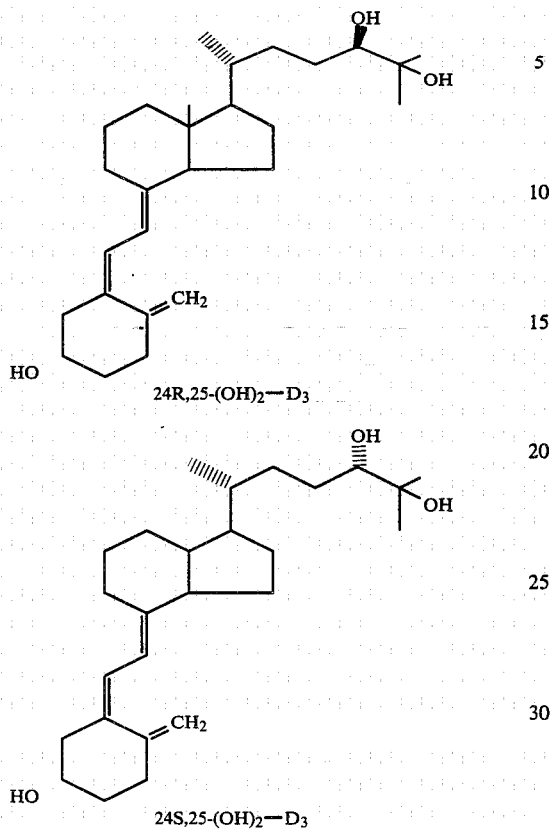

Namely, 24,25-dihydroxycholecalciferol may be 24R,25-$(OH)_2$-$D_3$, 24S,25-$(OH)_2$-$D_3$ or a mixture thereof, however, in particular, it is preferably 24R,25-$(OH)_2$-$D_3$.

The pharmaceutical composition according to the present invention for the treatment of pains and pyrexia, hypertension, hypotension, hyperlipemia, inflammatory diseases, or diseases due to the functional accentuation of the thrombocytes comprises an effective amount of the above-mentioned substance as an active ingredient and a carrier or diluent therefor, is used in dosage unit form with various types of formulation, and can be administered orally or parenterally (including rectal route), however, oral administration thereof is preferable.

The pharmaceutical composition containing 24,25-$(OH)_2$-$D_3$ as an active ingredient is used as an administrative form such as tablet, powder, granule, suppository, encapsulation, solution in alcoholic medium or in oily medium and aqueous suspension. As the oily medium, triglycerides of $C_8$ to $C_{10}$ fatty acid, corn oil, cotton seed oil, peanut oil, fish-liver oil, cacao bean oil or glycerol is preferably used.

In addition, as the other component, lactose, starch, talc, magnesium stearate, sorbic acid, sorbate salts, sugars and sugar alcohols, physiological saline solution, surfactant, anti-oxidant or other medicine can be admixed with 24,25-$(OH)_2$-$D_3$.

The pharmaceutical composition according to the present invention may contain, in unit dosage form thereof, $2 \times 10^{-5}$ to 4% by weight, preferably $2 \times 10^{-4}$ to 1% by weight of 24,25-$(OH)_2$-$D_3$, and 24,25-$(OH)_2$-$D_3$ is administered to an adult patient at a daily dose of 0.1 to $1 \times 10^5$ µg, preferably 0.5 to $1 \times 10^4$ µg.

The results of examination of the acute toxicity of 24,25-$(OH)_2$-$D_3$ are shown as follows.

An ethanolic solution of 24R,25-$(OH)_2$-$D_3$ or 24S,25-$(OH)_2$-$D_3$ was dissolved into triglyceride of $C_8$ to $C_{10}$ fatty acid to prepare a specimen containing 2% by weight of ethanol.

The thus prepared specimen was orally administered once to each of a group of ten male ICR-mice of body weight of 25±3 g at a dosage of 100 mg/kg body weight. Observation of the thus treated mice on their symptoms of intoxication for 2 weeks after the administration gave no abnormal findings on the mice without any death.

The results of examinations carried out after sacrificing each of the mice, including blood examination, biochemical examination, autopsy and pathohistological examination, were the same as those obtained on the mice to which the triglyceride of the fatty acid only containing 2% by weight of ethanol was administered.

Accordingly, since the $LD_{50}$ acute oral of 24R,25-$(OH)_2$-$D_3$ was larger than 100 mg/kg of the body weight of each mouse, and the same results were obtained by the administration of 24S,25-$(OH)_2$-$D_3$ in the same manner as above, it can be said that the present substance is quite safe as compared to 1α-(OH)-$D_3$ which is called as an active type of vitamin $D_3$ and shows a $LD_{50}$ acute oral of less than 1 mg/kg body weight.

The present invention will be explained more in detail while referring to the following examples in which 24R,25-$(OH)_2$-$D_3$ was used, the confirmation of the structure of the optical isomer due to 24 position having been carried out following "Tetrahedron Letters", No. 6, pages 2203 to 2206, 1975.

The present invention is explained in more detail in the following Examples; however, it should be recognized that the scope of the present invention is not restricted to these Examples.

EXAMPLE 1

Antipyretic and sedative activity of the present substance

Sedative activity

On mechanically stimulated animals by pressure:

Test animals were selected from female ICR mice by giving a pressure on the root of a tail of each animal while using a pressure-stimulating apparatus of Takagi and Kameyama (manufactured by Natsume Works) and picking up the individual which showed the threshold value of the pain in a range of from 50 to 80 mmHg. The thus selected test animals were divided into groups each consisting of 10 animals.

A solution of 24R,25-$(OH)_2$-$D_3$ in triglyceride of $C_8$ to $C_{10}$ fatty acid was orally adminstered to each test animal at a dose rate of 100 micrograms/kg body weight, and the thus treated animal was subjected to the above-mentioned mechanical stimulation repeatedly with the passage of time while raising the pressure until the test animal showed the pseudo-escaping reaction. The pressure applied at the time of pseudo-escaping and the time (sec) until the pseudo-escaping reaction was shown were recorded as shown in Table 1 and used as the factors in judging the sedative effect of 24R,25-$(OH)_2$-$D_3$.

TABLE 1

| Group | Pressure (mmHg) applied at the onset of pseudo-escaping reaction | Time (sec) until the onset of pseudo-escaping reaction |
| --- | --- | --- |
| Test group | 82 | 37 |
| Control group | 66 | 30 |

On Chemically stimulated animals:

Female ICR mice after 5 to 6 weeks of their birth were divided into groups each consisting of 10 animals, and they were subjected to a test following the method of Kostet et al. (1959) as follows.

After 6 hours of an oral administration of a solution of 24R,25-$(OH)_2$-$D_3$ in triglyceride of $C_8$ to $C_{10}$ fatty acid to each of the mice of each group at a dose rate of 100 micrograms/kg body weight, an aqueous 0.6% solution of acetic acid was intraperitoneally injected to each of the thus treated mice at a dose rate of 0.1 ml/10 g body weight. From the time after 10 min of the injection, the number of writhing observed on the mice was counted for 10 min, and the rate (%) of suppressing the stimulation by acetic acid was obtained while using the following formula as compared to the number of writhing observed on each mouse of the control group to which only the triglyceride and the solution of acetic acid were administered.

Rate of suppressing the stimulation (%)=$(1-T/C)\times 100$ wherein T is the mean number of writhing on the test group and C is the mean number of writhing on the control group.

The test results are shown in Table 2 wherein the rate of suppressing the stimulation is referred to as I.R. (%).

TABLE 2

| Group | Amount of the present substance admin. | I.R. (%) |
| --- | --- | --- |
| Test | 100 μg/kg | 29.0 |
| Control | — | 0.0 |

Antipyretic activity

The test was carried out following the method of Winter et al. (1961) as follows.

Each of six rats constituting a group was administered subcutaneously with an aqueous 20% suspension of beer-yeast, and after 19 hours of fasting, a solution of 24R,25-$(OH)_2$-$D_3$ in triglyceride of $C_8$ to $C_{10}$ fatty acid was orally administered to the thus treated and fasted rats at a dose rate of 100 micrograms/kg body weight.

Each of six rats constituting another group was administered the same aqueous solution of beer yeast, however, after 19 hours of fasting, only the same triglyceride was orally administered as the treated control, and each of six rats constituting still another group was used as control without specifically treated.

The rectal temperature of each of the above-mentioned three groups was measured with the passage of time, and the minimum rectal temperature of the test animal shown at the time when the activity of 24R,25-$(OH)_2$-$D_3$ showed the maximum was recorded. The rectal temperature of the treated control and that of the control at the above-mentioned time were also recorded.

The rate of suppressing the raising of the rectal temperature, i.e., the rate of suppressing pyrexia (referred to as I.R. (%)), was obtained by the following formula:

$$I.R.\ (\%) = \frac{C_1 - T}{C_1 - C_2} \times 100$$

wherein T is the average rectal temperature of the test group, $C_1$ is the average rectal temperature of the treated control group and $C_2$ is the average rectal temperature of the control not specifically treated.

The thus obtained rate of suppressing pyrexia caused by beer yeast and suppressed by 24R,25-$(OH)_2$-$D_3$ was 36.8%.

EXAMPLE 2

Blood pressure reducing activity

A solution of 24R,25-$(OH)_2$-$D_3$ in triglyceride of $C_8$ to $C_{10}$ fatty acid was orally administered to each of ten rats as a group, which were suffering from hypertension spontaneously, at a dose rate of 100 micrograms/kg body weight. After 6 and 12 hours of the administration, the blood pressure of each of the thus treated rats was measured while using a tonometer (manufactured by Ueda Works, the model USM-105R), and the difference between the blood pressure before administration and that after 9 and 12 hours of the administration was evaluated as the effectiveness of 24R,25-$(OH)_2$-$D_3$ as a hypotensor while using the rats to which only the triglyceride was administered as the control.

The results of the test are shown in Table 3.

TABLE 3

| Group | Amount of administration | Hypotensive effect (mmHg) after 9 hours | Hypotensive effect (mmHg) after 12 hours |
| --- | --- | --- | --- |
| Test group | 100 μg/kg | 12 | 19 |
| Control | — | 1 | 2 |

Also in the test similarly carried out while 24S,25-$(OH)_2$-$D_3$, nearly the same result was obtained.

Namely, every one of 24,25-$(OH)_2$-$D_3$ clearly showed a blood pressure reducing activity thereby demonstrating the effectiveness thereof as a hypotensor.

EXAMPLE 3

Activity of reducing the lipid level in blood

After feeding a group of male Japanese white rabbits with a solid feed stuff (CR-1) containing 1% of cholesterol for about 3 months ad lib. and confirming the raise of the lipid level in the blood thereof, the following test was carried out while using the thus treated animals as the model animals of hyperlipemia.

A solution of 24R,25-$(OH)_2$-$D_3$ in triglyceride of $C_8$ to $C_{10}$ fatty acid was orally administered to each of the animal at a dose rate of 100 micrograms/kg body weight, and the blood specimen was taken with the passage of time to be analyzed for the lipid in the serum, namely the total cholesterol level therein by the enzymic method and the β-lipoprotein therein by the turbidimetric method. The results are shown in Table 4 below.

TABLE 4

| Group | Amount decreased or increased of β-lipoprotein 6 hours* | Amount decreased or increased of β-lipoprotein 12 hours* | Amount decreased or increased of Cholesterol 6 hours* | Amount decreased or increased of Cholesterol 12 hours* |
| --- | --- | --- | --- | --- |
| Test group | 140 | 148 | 2 | 51 |

TABLE 4-continued

| Group | Amount decreased or increased of | | | |
|---|---|---|---|---|
| | β-lipoprotein | | Cholesterol | |
| | 6 hours* | 12 hours* | 6 hours* | 12 hours* |
| Control** | 5 | −2*** | −3 | 9 |

Notes:
*time after the administration
**the groups fed with CR-1, however, not administered
***the sign of (−) shows the increase of the level.

From the toxicological property and the pharmacological result described above, it is understood that 24R,25-(OH)$_2$-D$_3$ can be practically utilized as an active ingredient of the anti-lipemic pharmaceutical composition and the pharmaceutical composition for treating anteriosclerosis.

EXAMPLE 4

Anti-inflammatory activity of the present substance

Activity of suppressing the edema caused by carrageenin

After 6 hours of forcible administration of a solution of 24R,25-(OH)$_2$-D$_3$ in triglyceride of C$_8$ to C$_{10}$ fatty acid orally to each of the group consisting of 10 rats at a dose rate of 100 microgram/kg while following the method of van Arman et al. (1963), an aqueous 1% suspension of carrageenin in aqueous physiological saline solution is injected to the sole of the right hind leg of each of the rats. The volume of the thus treated sole was determined with the passage of time after the injection to obtain the rate of suppressing of the edema due to the injection of carrageenin while using the following formula:

$$\text{Rate of suppression } (I.R.(\%)) = (1 - T/C) \times 100$$

wherein T is the average volume of the sole of the leg and C is the average volume of the sole of the leg of the control rat of which the triglyceride was administered instead of the solution of 24R,25-(OH)$_2$-D$_3$ in the triglyceride.

As a result, it was found that the rate of suppressing the edema due to carrageenin of 24R,25-(OH)$_2$-D$_3$ was 15.4%.

Activity of suppressing the formation of granuloma

After subcutaneously injecting air into the back of each of 6 rats constituting a group to form a pouch and 0.5 ml of a 1% solution of croton oil in sesame oil was injected into the pouch. Then, a solution of 24R,25-(OH)$_2$-D$_3$ in triglyceride of C$_8$ to C$_{10}$ fatty acid was orally administered to each of the thus treated rat continuously for 5 days at a daily dosage of 10 micrograms/kg body weight. On the 6th day, the amount of the liquid exuded into the pouch was measured, and applying the data together with the data obtained on the control animal to which the triglyceride was injected instead of the solution in triglyceride to the same formula, the rate of suppression of the formation of granuloma was obtained. The rate of suppression by 24R,25-(OH)$_2$-D$_3$ was 17.8%, showing the effectiveness of 24R,25-(OH)$_2$-D$_3$ as an anti-inflammatory agent.

EXAMPLE 5

Inhibitory activity on agglutination of rat thrombocytes

The effect of 24R,25-(OH)$_2$-D$_3$ on the agglutination of thrombocytes induced by adenosine diphosphate (hereinafter referred to as ADP) was examined in vitro while using a platelet-rich plasma (hereinafter referred to as PRP) obtained from normal male Wistar rats after 20 weeks of birth, as follows.

Blood collecting with the addition of citrate in an amount of 1/9 of the total blood collected was carried out from the rats and the thus collected blood specimen was subjected to centrifugation for 6 min at 1,500 rpm to obtain a supernatant liquid, which was used as PRP.

To 250 ml of PRP, 1.5 microliters of an ethanolic solution of 24R,25-(OH)$_2$-D$_3$ at a concentration of 2 mg/ml were added, and after incubating the mixture for 2 min at 37° C., 30 micromol of ADP was added to the incubated mixture, and the thus obtained mixture was subjected to determination of the rate of agglutination while using Payton Lumiaggregation Module Model 1000 as the apparatus for observing the function, the final concentration of 24R,25-(OH)$_2$-D$_3$ being 12 microgram/ml of the mixture of PRP and the ethanolic solution of 24R,25-(OH)$_2$-D$_3$ and the concentration of ethanol in the mixture being 0.6%. As a control, a mixture of 250 ml of PRP and 1.5 microliters of ethanol containing 0.6% of ethanol was used.

The rate of inhibition (I.R.(%)) by 24R,25-(OH)$_2$-D$_3$ of the agglutination of thrombocytes in PRP induced by ADP was obtained from the following formula:

$$I.R. \ (\%) = \frac{C - T}{C} \times 100$$

wherein C is the maximum rate of agglutination in the control and T is the maximum rate of agglutination in the specimen to which 24R,25-(OH)$_2$-D$_3$ had been added.

In the present test, C was 44.5(%) and T was 37.0(%), and accordingly, I.R.(%) of 24R,25-(OH)$_2$-D$_3$ was about 17.0%.

EXAMPLE 6

Inhibitory activity on agglutination of human thrombocytes

The effect of 24R,25-(OH)$_2$-D$_3$ on the agglutination of human thrombocytest induced by ADP was examined in a similar manner as in Example 5 while using PRP obtained from a fresh blood taken from the vein of a healthy person, the final concentration of 24R,25-(OH)$_2$-D$_3$ in the treated specimen being 1 microgram/ml and the amount of ADP being 5 micromol.

As a result of the examination, it was found that the rate of inhibition by 24R,25-(OH)$_2$-D$_3$ of the agglutination of human thrombocytes induced by ADP was 37.6%.

EXAMPLE 7

Inhibitory activity on agglutination of thrombocytes of a rat suffering from diabetes mellitus induced by STZ The effect of 24R,25-(OH)$_2$-D$_3$ in inhibiting the agglutination of thrombocytes in PRP taken from the rats suffering from artificial diabetes mellitus induced by streptozocin and those in PRP taken from the normal rats was examined as follows.

After 48 hours of fasting of male Wistar rats in 6th week after birth, streptozocin was intraperitoneally administered to each rat at a dose rate of 65 mg/kg body weight, and after one week of the administration, blood specimen was taken from the caudal vein of each rat to test the concentration of blood sugar therein and the concentration of glucose in urine of the rat.

The rats showing the blood sugar level of 500 to 600 mg/ml and the urinal excretion of glucose of ++++(2%) on Hemaconbistiz III test paper (Miles.-Sankyo Co., Ltd.) were taken as the test animals suffering from diabetes mellitus, and blood collecting was carried out from these rats and the normal rats (not administered with streptozocin) while using citrate in blood collecting.

PRP prepared from the thus collected blood in the same manner as in Example 7 was further diluted with the addition of PPP (platelet poor plasma, obtained by subjecting the remainder of preparation of PRP to centrifugal separation for 10 min at 3,000 rpm) to obtain the diluted PRP containing 300,000 thrombocytes in $mm^3$. The amount of ADP (coagulant) was 30 micromol.

The result of examination is shown in Table 5. For reference, in the present test, the final concentration of 24R,25-(OH)$_2$-D$_3$ in the mixture of the diluted PRP and the ethanolic solution of 24R,25-(OH)$_2$-D$_3$ is also shown in Table 5. As a control, the mixture of the diluted PRP and ethanol was used.

TABLE 5

Effect of 24R,25-(OH)$_2$—D$_3$ on thrombocytes in PRP taken from the rats suffering from artificial diabetes mellitus

| Effect | Concentration of 24R,25-(OH)$_2$—D$_3$ (ng/ml) | | | |
|---|---|---|---|---|
| | 0* | $1 \times 10^{-2}$ | 1.0 | $1 \times 10^{+2}$ |
| Maximum rate of agglutination of thrombocytes (%) | 47.8 | 35.8 | 38.2 | 40.4 |
| Rate of inhibition on agglutination of thrombocytes (%) | 0 | 25.1 | 20.1 | 15.5 |

Note:
*Control, PRP containing 0.6% of ethanol

In addition, the effect of 24R,25-(OH)$_2$-D$_3$ in inhibiting the agglutination of thrombocytes induced by 30 micromol of ADP in the diluted PRP (containing 300,000 thrombocytes in $mm^3$ thereof) prepared from the blood taken from the normal rat was examined to show the maximum rate of agglutination of thrombocytes of 15.0 to 17.0% irrespective of the concentration of 24R,25(OH)$_2$-D$_3$.

As are seen in Table 5, the inhibiting effect of 24R,25-(OH)$_2$-D$_3$ on the agglutination of thrombocytes induced by ADP in the PRP prepared from the blood taken from the rats suffering from diabetes mellitus induced by streptozocin showed an increase with the raise of the concentration of 24R,25-(OH)$_2$-D$_3$ and after showing a peak (not shown in Table 5), gradually decreased, however, the effect was still large, for instance, the rate of inhibiting the agglutination of thrombocytes was 25.1% at a low concentration of $1\times10^{-2}$ ng/ml.

EXAMPLE 8

Inhibitory activity on agglutination of thrombocytes of a rat suffering from hereditary hypertension The effect of 24R,25-(OH)$_2$-D$_3$ in inhibiting the agglutination of the thrombocytes in PRP collected from the blood taken from the rats suffering from hereditary hypertension (the model animal of spontaneous hypertension, hereinafter referred to as SHR rats) was examined as follows.

Blood was collected from each abdominal aorta of the SHR rats in 7 to 8 weeks after birth while using citrate, and PRP was prepared from the thus collected blood to examine the agglutination of thrombocytes in PRP as in Example 8, the final concentration of 24R,25-(OH)$_2$-D$_3$ being 1 ng/ml of PRP taken from the test animal, and ethanol being added to PRP taken from normal animals, instead of the ethanolic solution of 24R,25-(OH)$_2$-D$_3$.

The rate of inhibition of 24R,25-(OH)$_2$-D$_3$ on the agglutination of thrombocytes induced by ADP was 18.3% as compared to control.

EXAMPLE 9

Inhibitory activity on agglutination of thrombocytes of rabbits suffering from experimental arteriosclerosis and hyperlipemia Male Japanese white rabbits were fed with a solid feed stuff containing 1% by weight of cholesterol ad lib. for 3 months, and after confirming the raise of the concentration of lipids in the serum thereof, the effects of 24R,25-(OH)$_2$-D$_3$ on the agglutination of the thrombocytes in PRP of the thus fed rabbit induced by ADP was examined while following the methods of preparation of PRP and the determination of the degree of agglutination shown in Example 9. The final concentration of 24R,25-(OH)$_2$-D$_3$ in the treated PRP was 1 ng/ml and the amount of ADP was 30 micromol. Ethanol was mixed instead of the ethanolic solution of 24R,25-(OH)$_2$-D$_3$ with PRP prepared from the blood taken from control (normal) animal.

As a result, it was found that 24R,25-(OH)$_2$-D$_3$ showed the rate of inhibition of 15.8% on the agglutination of thrombocytes in PRP from the treated rabbit induced by ADP.

EXAMPLE 10

Inhibitory activity on agglutination of thrombocytes of the model animal suffering from renal failure Male Wistar rats after 6 weeks of birth were subjected to complete nephrectomy and after confirming the noticeable raise of serum BUN (urea nitrogen in serum) thereof on the 3rd day of the operation, the effect of 24R,25-(OH)$_2$-D$_3$ on the agglutination of thrombocytes in PRP prepared from the blood of the thus treated rat induced by ADP was examined while using the thus treated rats as model animals of renal failure and following the methods of preparing PRP and the determination of the degree of agglutination of the thrombocytes shown in Example 10. The final concentration of 24R,25-(OH)$_2$-D$_3$ in the treated PRP was 1 ng/ml, and the amount of ADP was 30 micromol. PRP of control animal was mixed with ethanol instead of the ethanolic solution of 24R,25-(OH)$_2$-D$_3$.

As a result, it was found that 24R,25-(OH)$_2$-D$_3$ showed the effect of inhibiting the agglutination of thrombocytes in PRP of the thus treated animal of 17.3%.

EXAMPLE 11

Anti-thrombotic activity of the present substance

Twenty male Wistar rats after 10 weeks of birth were divided equally into two groups, and a solution of 24R,25-(OH)$_2$-D$_3$ in triglyceride of C$_8$ to C$_{10}$ fatty acid was forcibly administered pro os to those of the first group, those of the other group being administered only with the triglyceride as a control group.

ADP was intravenously injected to all the rats after 6 hours of the administration.

As a result, all the rats of the control group died, however, the mortality of those of the first group to which 24R,25-(OH)$_2$-D$_3$ had been administered was 63%.

The results show the anti-thrombotic function of 24R,25-(OH)$_2$-D$_3$.

EXAMPLE 12

Preparation of a pharmaceutical composition containing the present substance as an active ingredient Into one kilogram of triglyceride of C$_8$ to C$_{10}$ fatty acid, into which gaseous argon had been bubbled for 72 hours under irradiation from a 400 W high pressure mercury lamp, thereby having eliminated peroxides originally contained therein, 5 mg of 24R,25-(OH)$_2$-D$_3$ were dissolved. The thus obtained solution and a wall component prepared by combining the following components under heating were subjected to a machine for producing soft capsules to obtain the soft-encapsulated pharmaceutical composition containing one, two, five or 10 micrograms of 24R,25-(OH)$_2$-D$_3$ in one capsule.

Recipe for soft capsule wall 10 parts by weight of gelatin,
2 parts by weight of glycerol,
0.05 part by weight of ethyl parahydroxybenzoate as an antiseptic,
0.2 part by weight of titanium white and
0.2 part by weight of water in the completed capsule.

What is claimed is:

1. A method for the treatment of hypertension, hypotension, hyperlipemia, or diseases due to the functional accentuation of thrombocytes, which comprises administering to a patient suffering from hypertension, hypotension, hyperlipemia, or diseases due to the functional accentuation of thrombocytes an effective amount of a compound of 24,25-dihydroxycholecalciferol.

2. A method according to claim 1, wherein said compound is 24R,25-dihydroxycholecalciferol.

* * * * *